(12) United States Patent
Nose et al.

(10) Patent No.: US 6,884,210 B2
(45) Date of Patent: Apr. 26, 2005

(54) BLOOD PUMP

(75) Inventors: Yukihiko Nose, Houston, TX (US);
Seiji Ichikawa, Houston, TX (US);
Toshiyuki Shinohara, Houston, TX (US)

(73) Assignees: Miwatec Incorporated, Kanagawa-ken (JP); Baylor College of Medicine, Houston, TX (US)

( * ) Notice: Subject to any disclaimer, the term of this patent is extended or adjusted under 35 U.S.C. 154(b) by 378 days.

(21) Appl. No.: 10/171,094

(22) Filed: Jun. 12, 2002

(65) Prior Publication Data

US 2003/0233021 A1 Dec. 18, 2003

(51) Int. Cl.[7] .................................................. F04D 7/02
(52) U.S. Cl. ........................................................... 600/16
(58) Field of Search .................................... 600/16–18

(56) References Cited

U.S. PATENT DOCUMENTS

| | | | |
|---|---|---|---|
| 5,399,074 A | 3/1995 | Nose et al. | |
| 5,399,145 A | 3/1995 | Ito et al. | |
| 5,575,630 A | 11/1996 | Nakazawa et al. | |
| 5,601,418 A | 2/1997 | Ohara et al. | |
| 5,683,231 A | 11/1997 | Nakazawa et al. | |
| 5,713,730 A | 2/1998 | Nose et al. | |
| 5,803,720 A | 9/1998 | Ohara et al. | |
| 6,183,220 B1 | 2/2001 | Ohara et al. | |
| 6,264,635 B1 | 7/2001 | Wampler et al. | |
| 6,717,311 B1 * | 4/2004 | Locke | 310/90.5 |
| 2001/0031210 A1 * | 10/2001 | Antaki et al. | 417/356 |

OTHER PUBLICATIONS

Maslen, Eric H., et al., "Feedback Control Applications in Artificial Hearts," *IEEE Control Systems Magazine*, vol. 18, No. 6, Dec. 1998, pp. 26–34.

* cited by examiner

*Primary Examiner*—Scott M. Getzow
(74) *Attorney, Agent, or Firm*—Barry R. Lipsitz; Douglas M. McAllister

(57) ABSTRACT

It is an object of the present invention to realize a small and light blood pump that can control thrombosis and moreover, endure a prolonged use.

A blood pump comprising an impeller, a casing having a suction inlet and a delivery outlet and rotatably encasing the impeller, a magnetic drive means for rotating the impeller by magnetically acting from outside of the casing on a magnet that the impeller includes, a magnetic attraction force adjustment means for adjusting the attraction force by said magnetic action, a control means for rotating speed of said magnetic drive means, and a pair of pivot bearings for supporting pivots at both ends of the impeller rotation shaft, wherein the distance between bearing faces of said both pivot bearings is set longer than the length of the rotation shaft of the impeller and the rotation speed of the impeller is controlled to a predetermined speed by said control means for rotating speed so as to levitate the impeller in the blood flow in the casing and to maintain out of contact between the pivots at both ends of the rotation shaft of the impeller and the bearing face of said both pivot bearing.

23 Claims, 5 Drawing Sheets

Impeller bottom face

Casing bottom face

BLOOD PUMP

BACKGROUND OF THE INVENTION

1. Field of the Invention

The present invention concerns a blood pump used for artificial heart-lung machine or the like, and more particularly, a centrifugal pump that can be operated with the rotation shaft out of contact in respect to the bearing by controlling the rotating speed.

2. Detailed Description of the Prior Art

Recently, studies for replacing or complementing a malfunctioning internal heart with an artificial heart have been conducted vigorously in Japan and abroad in past several decades. As important problems for the practical use of artificial heart, first, we can name the prevention of thrombosis from occurring in the artificial heart. In addition, improvement of durability of artificial heart is also an essential problem to be resolved for the practical use thereof.

Initially, the research and development of artificial heart have been conducted mainly for pulsation type pumps such as bellows pump or the like having pulsation function similar to the human heart; however, in recent years, a continuous flow type centrifugal pump without pulsation attracts attention, because the miniaturization is easy, and moreover, the structure is simple and the durability is excellent.

In short, various research and development are being conducted concerning the centrifugal pump, because it has been demonstrated that the centrifugal pump is appropriate for use as complementary means of an original heart by disposing in the body in parallel with the original heart, because it can be reduced easily in size and weight, or, that the organism can cope with the fluid transferred by the pump even if the fluid is continuous, thanks to physiological factors of the human body, or others.

For example, in Japan, an external auxiliary circulating pump using a centrifugal pump, having cleared the legal review, is in the phase of practical use. This external auxiliary circulating pump, supposing a usage duration of one month or less, the occurrence of thrombosis is not so problematic.

On the other hand, researches for practical use of pulsation type pump are active, and 7 clinical examples of integral implantation of artificial heart with pulsation type pump have been reported in 2001.

Nonetheless, it is difficult to miniaturize the pulsation type artificial heart and, consequently, the pulsation type artificial heart is limited to the application for adults of 85 Kg or more in weight. On the contrary, the continuous flow artificial pump with centrifugal pump can be miniaturized easily and has an advantage that it is not particularly necessary to limit physically patients to whom it is applied.

A number of prior arts have been disclosed, concerning the continuous flow type blood pump by a centrifugal pump; however, actually, it can not be the that the following two problems are solved for a prolonged use.

Namely:

(a) Control of thrombosis occurrence.

(b) Sustention of stable rotation by preventing the rotation shaft from wear in the bearing section.

SUMMARY OF THE INVENTION

The present invention is intended to solve the above-mentioned conventional situation and, an object of the present invention is to solve the aforementioned conventional problems by a blood pump comprising:

an impeller, a casing having a suction inlet and a delivery outlet and rotatably encasing the impeller, a magnetic drive means disposed outside the casing for rotating the impeller by magnetically acting on a magnet that the impeller includes, a magnetic attraction force adjustment means for adjusting the attraction force by the magnetic action, a control means for rotation speed of the magnetic drive means, and a pair of pivot bearings for supporting pivots at both ends of the impeller rotation shaft, wherein the distance between bearing faces of the both pivot bearings is set longer than the length of the rotation shaft of the impeller and the rotation speed of the impeller is controlled to a predetermined speed by the control means for rotation speed so as to levitate the impeller in the blood flow in the casing and to maintain out of contact between the pivots at both ends of the rotation shaft of the impeller and the bearing face of the both pivot bearing.

In the aforementioned blood pump, the difference between the distance between the bearing faces of the both pivot bearings and the length of the rotation shaft of the impeller may be sometimes set to 0.4 mm or longer.

In addition, in one of the aforementioned blood pumps, the casing and impeller may sometimes be formed of titanium or titanium alloys, and the surface roughness of titanium or titanium alloys at the points in contact with blood in the casing or impeller be polished to 0.5 micron or less.

Further, in one of the aforementioned blood pumps, the suction inlet may sometimes be composed of a pipe made of titanium or titanium alloys having a predetermined angle with the rotation shaft of the impeller and connected to the casing upper section, and the surface roughness of the pipe inner surface be polished to 0.5 micron or less.

Furthermore, in one of the aforementioned blood pumps, the bearing surface of the pair of pivot bearing supporting the pivots at both ends of the rotation shaft of the impeller may sometimes be formed of ultra high polymer material.

Or, in one of the aforementioned blood pumps, the pivots at both ends of the rotation shaft of the impeller may sometimes be formed of ceramics.

And, in one of the aforementioned compositions, the curvature of the bearing surface of the pivot bearing section may sometimes be set larger than the curvature of the pivot of the rotation shaft of the impeller.

The impeller rotating speed is required to be set according to the necessary blood flow rate; however, the rotating speed is also closely connected to the levitation of the impeller, namely to make the pivot shafts at both ends of the rotation shaft of the impeller out of contact with the bearing surface of the pivot bearing, making difficult to set a rotating speed will realize the levitation of the impeller together the maintenance of the predetermined blood flow rate. Consequently, in the concerned embodiment, the desired rotating speed is intended to be set according to the indicator established based on the data found preliminarily by experiment. In this case, the indicator means also the one written in a computer program integrated as firmware in the control means for pump drive.

As for the material composing the pump, the biocompatibility is increased by using pure titanium or titanium alloys such as Ti4Al6V for the necessary points, and furthermore, thrombosis is prevented from occurring for a long time by polishing the surface in contact with blood in the pump to a surface roughness equal or inferior to 0.5 µm, preferably, equal or inferior to 0.2 µm.

In the invention of the present application, the pivot shaft of the rotation shaft of the impeller and the bearing surface of the pivot bearing are out of contact when the impeller is levitated, but they come into contact inevitably when the rotation starts and terminates. In order to prevent the wear during this contact, the bearing surface is formed with polymer material such as polyethylene and the impeller rotation shaft including the pivot section uses ceramics such as high-purity alumina sinter material.

For the levitation of the impeller, a clearance is required between the impeller rotation shaft length and the distance between the pair of bearing surfaces; however, if the value of clearance is too small, blood stagnates and makes difficult to prevent the thrombosis. On the other hand, if the set value of clearance is too large, the support of shaft by the bearing becomes unstable. According to the experiment, it is estimated that the clearance value C is most preferably in a range of $0.4 \text{ mm} \leq C \leq 1 \text{ mm}$, in view of thrombosis prevention effect, impeller stable levitation, prevention of dislocation of the pivot shaft from the bearing or others.

According to the experimental data, the rotating speed of the impeller, the clearance and the behavior of the impeller in the casing shows substantially the following relation, and the larger is the value of clearance, the larger is the range of rotating speed where the impeller levitation can be maintained.

A: In case of clearance=0.4 mm:

(a) 1 0 0 0 rpm: The impeller does not levitate; consequently, the lower end pivot shaft of the rotation shaft and the bearing surface are in contact, while the upper end pivot shaft are out of contact with the bearing surface.

(b) 1 4 0 0 rpm: The impeller levitates, and upper and lower pivot shafts are out of contact with the bearing surface.

(c) 1 6 0 0 rpm: The impeller levitates, and upper and lower pivot shafts are out of contact with the bearing surface. The distance between the impeller lower end and the casing bottom section increases than the (b), however, this distance does not attain yet the value of clearance, 0.4 mm.

(d) 1 8 0 0 rpm: The impeller goes up from the position of the (c) and the upper end pivot shaft is in contact with the bearing surface. Consequently, the distance between the lower end pivot shaft and the bearing surface is theoretically equal to the value of clearance, 0.4 mm; however, in practice, the distance between the lower end pivot shaft and the bearing surface is not always kept to 0.4 mm, because the upper end pivot shaft and the bearing surface comes into and out of contact repeatedly.

B: In case of clearance=1.00 mm:

(a) 1 0 0 0 rpm: The impeller does not levitate; consequently, the lower end pivot shaft of the rotation shaft and the bearing surface are in contact, while the upper end pivot shaft are out of contact with the bearing surface.

(b) 1 4 0 0 rpm: The impeller levitates, and upper and lower pivot shafts are out of contact with the bearing surface.

(c) 1 6 0 0 rpm: The impeller levitates, and upper and lower pivot shafts are out of contact with the bearing surface. The distance between the impeller lower end and the casing bottom section increases than the (b), however, this distance does not attain yet the value of clearance, 1.00 mm.

(d) 1 8 0 0 rpm: The impeller still levitates, and upper and lower pivot shafts are out of contact with the bearing surface. The distance between the impeller lower end and the casing bottom section increases further than the (c), however, this distance does not attain yet the value of clearance, 1.00 mm.

(e) 1 8 0 0 rpm: The impeller still goes up from the position of the (d) and the upper end pivot shaft is in contact with the bearing surface. Consequently, the distance between the lower end pivot shaft and the bearing surface is theoretically equal to the value of clearance, 1.00 mm; however, in practice, the distance between the lower end pivot shaft and the bearing surface is not always kept to 1.00 mm, because the upper end pivot shaft and the bearing surface comes into and out of contact repeatedly.

The impeller levitation can be controlled only by the rotating speed of the impeller as mentioned above, in short, only by setting the rotating speed of the magnetic driving means to a predetermined value, so a special means for levitating the impeller is unnecessary. The control means for rotating speed of the magnetic driving means is different according to the rotation driving means (electric motor) provided in the magnetic driving means; in case of adopting an AC motor such as synchronous motor, induction motor or the like, it shall be composed of an inverter circuit and, in case of DC brushless motor, it shall be composed of a control of rotating speed by switching such as Pulse Width Modulation or the like, or a small and light circuit such as Phase Locked Loop or the like.

The impeller in the casing is composed to be coupled and rotated through the bottom wall of the casing by a magnetic driving means outside the casing and a so-called magnet coupling, and the magnetic attraction force between the impeller and the magnetic driving means is constant.

As the impeller levitates against this magnetic attraction force, it is desirable to dispose a magnetic attraction force adjustment means for adjusting the balance between the magnetic attraction force and the levitation force in order to control the behavior of the impeller in the casing. The impeller can prevent blood from stagnating by behaving up and down in the casing through the control of rotating speed, and this up and down behavior can be controlled more easily by controlling the balance.

The pipe as suction inlet to be attached to the casing upper section has a bent section from the anatomical view of the pump in an organism or from the hydrodynamic or physiological point of view of blood flowing in the casing. A structure wherein the inlet entrance portion would not physically damage tissues shall be adopted.

When the curvature radius of the bearing surface of the pivot bearing section is set to substantially two times or more of the curvature radius of the pivot of the impeller rotation shaft, the pivot shaft of the impeller titubates and rotates around the center of the bearing under predetermined conditions in the pivot bearing, allowing thereby the impeller to titubate (swerve) in the lower portion also, and resolving blood stagnation especially in the casing bottom section.

DETAILED DESCRIPTION OF THE INVENTION

Figure 1:
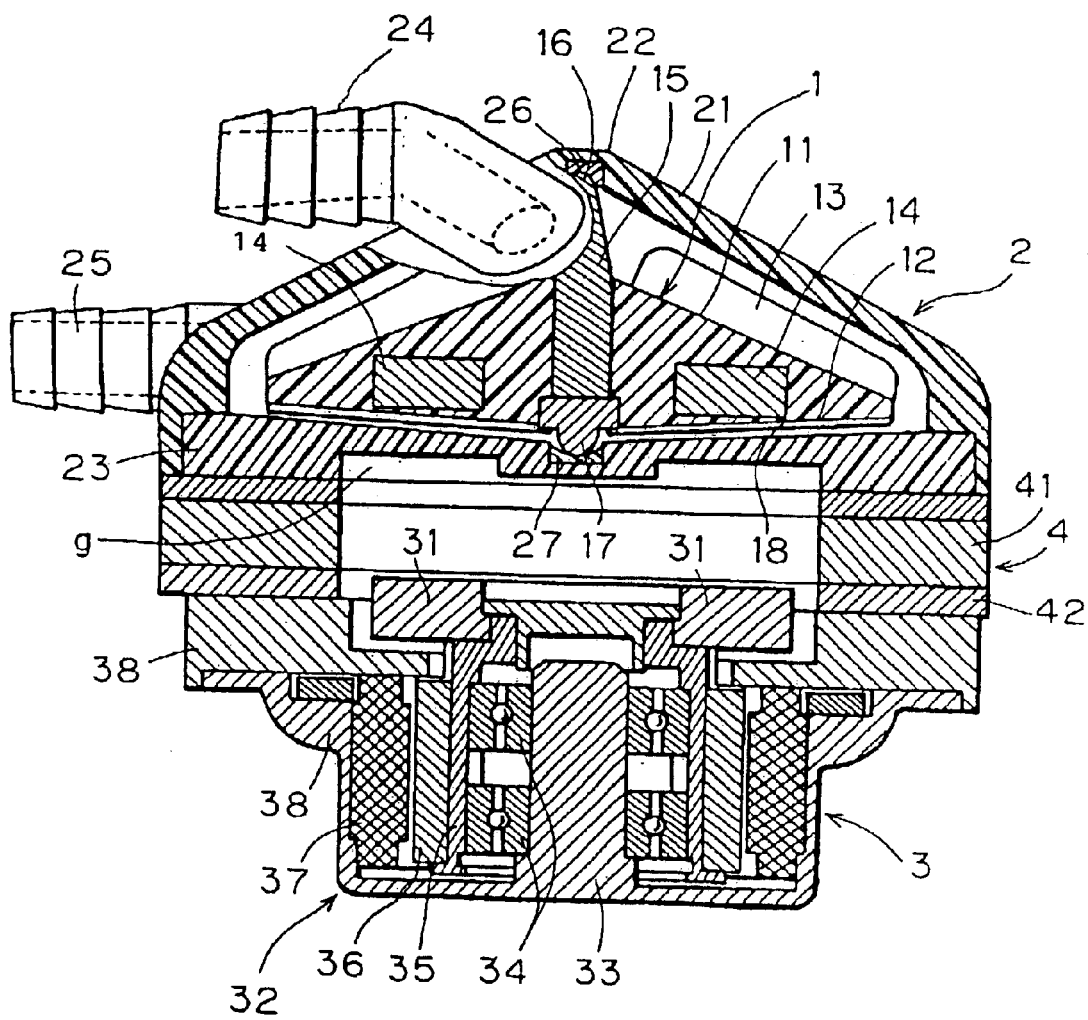
FIG. 1 is a longitudinal section view of a blood pump according to one embodiment.

Embodiments of the invention of the application shall be described based on drawings. FIG. 1 is a longitudinal section view of a blood pump according to one embodiment.

In the drawing, 1 represents a conical shape impeller, 2 a casing rotatably encasing the impeller, 3 a magnetic driving means placed under the casing 2, and 4 a magnetic attraction force adjustment means interposed between the casing 2 and the magnetic driving means 3. An outlier portion 38 of impeller 1, casing 2 and magnetic driving means 3 is formed of pure titanium or titanium alloys such as Ti4A16V, organic compatible materials, and furthermore, potions in contact with blood such as face side surface of the impeller, inner wall section of the casing 2 or others has a polished surface presenting a roughness equal or inferior to 0.2 $\mu$m in order to control the adhesion of platelet.

A side section 11 of the impeller 1 is provided with vanes 13, for discharging from a delivery outlet 25 blood flowing in from a suction inlet 24 of the casing 2 according to the rotation of the impeller 1.

A plurality of magnets 14 are embedded in the bottom section 12 of the impeller 1, for rotating the impeller 1 in cooperation with the magnetic driving means 3.

At the upper and lower end sections of a rotation shaft 15 of the impeller 1, a pivot shaft 16 and a pivot shaft 17 are formed, and respectively, they engage loosely with an upper pivot bearing 26 and a lower pivot bearing 27.

Figure 2:
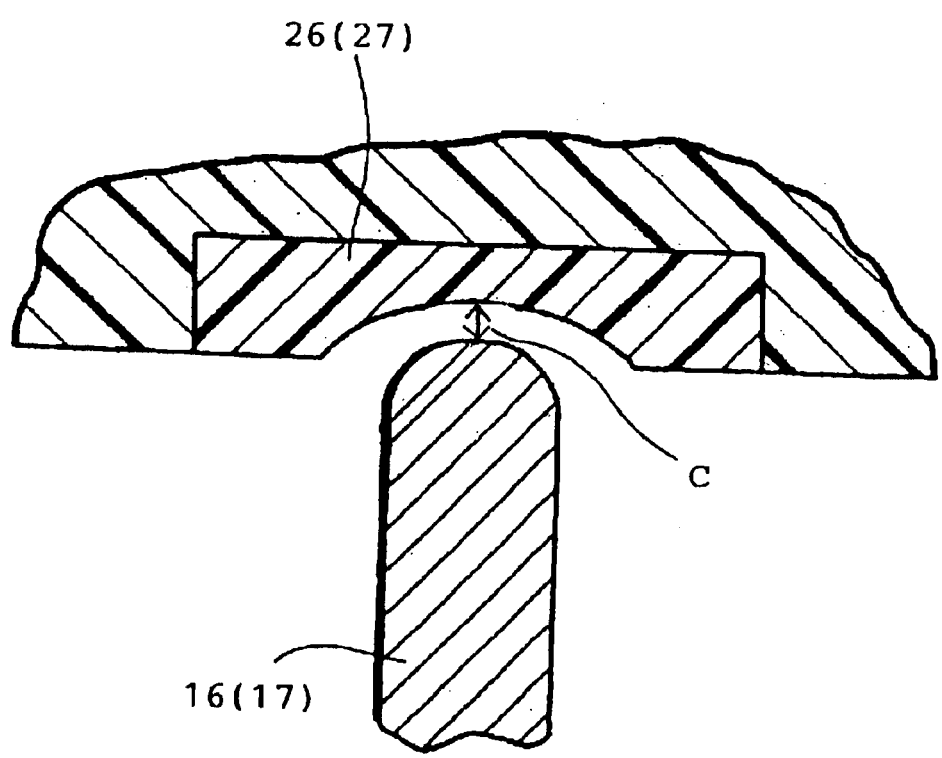
FIG. 2 is a section view showing a clearance between an impeller rotation shaft (pivot shaft) and a bearing.

As shown in FIG. 2, in a resting state of the impeller 1, a predetermined clearance C is formed between the upper end of the pivot shaft 16 and the bearing surface of the upper pivot bearing 26, and is set to C=0.6 mm in this embodiment. In short, the length of the rotation shaft 15 of the impeller 1 is shorter of 0.6 mm than the distance between the bearing surface of the upper pivot bearing 26 and the lower pivot bearing 27. It should be appreciated that the experimental results show that the thrombosis prevention effect falls dramatically when the clearance value C is inferior to 0.4 mm.

Figure 3:
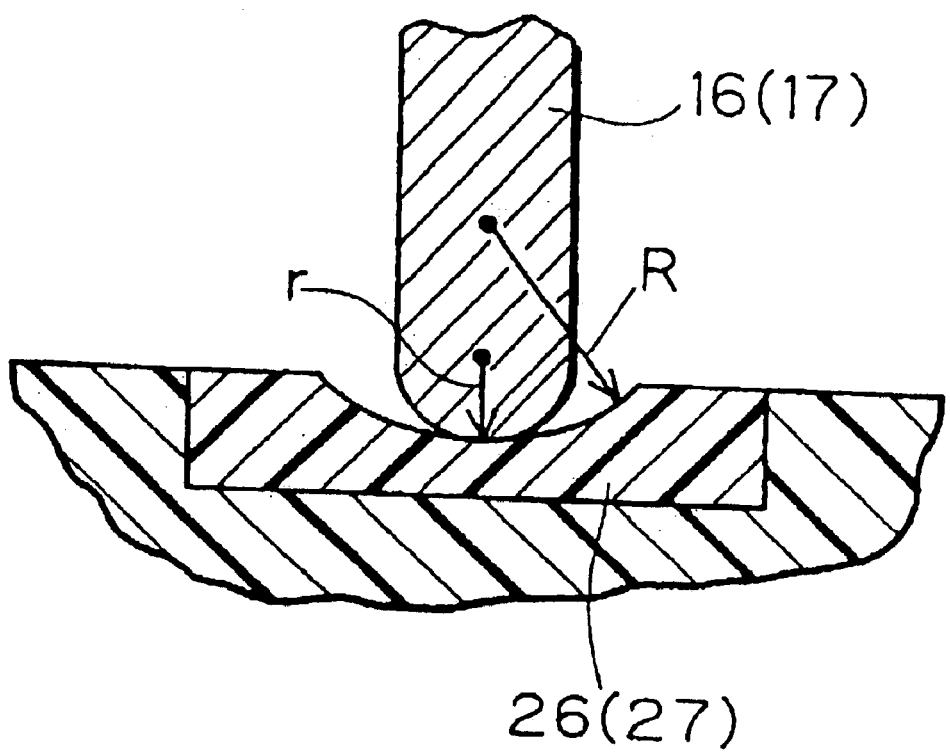
FIG. 3 is an enlarged section of a pivot shaft and a pivot bearing.

It should be appreciated that, in this embodiment, as shown in FIG. 3, the curvature radius R of the bearing surface of the pivot bearings 26, 27 is set to two times of the curvature radius r of the pivot shafts 16, 17, allowing thereby the pivot shaft to titubate (swerve) in the bearing surface more easily.

In addition, though the pivot shafts 16 and 17 of the rotation shaft 15 are formed of ceramic material, only the surface may be clad with ceramics. On the other hand, the bearing surface of the upper pivot bearing 26 and the lower pivot bearing 27 is formed with polymer material such as polyethylene or others.

Further, in FIG. 1, 24 indicates a pipe as suction inlet adhered to the upper section of a cone shaped casing 2, and made of a horizontal base 24a and an opening section 24b which is going to bend, the opening section 24b protrudes substantially parallel to the inner wall face of a slant section 21 of the casing 2 and a slant section 11 of the impeller 1 in the casing 2, whereby, blood sucked form the suction inlet 24 hits the rotation shaft 15, the inner wall face of the slant section 21, the slant section 11 of the impeller 1 or others, in a way to prevent hemolysis from occurring. In addition, 25 indicates a pipe as delivery output mounted horizontally to the slant section 21 of the casing 2.

The both pipes composing the suction inlet 24, and delivery outlet 25 are formed of pure titanium or Ti4A16V which is a titanium alloys, and have a polished surface presenting a roughness equal or inferior to 0.2 $\mu$m on the inside in contact with blood in order to control the adhesion of platelet.

Further, in FIG. 1, the magnetic driving means 3 provided under the casing 2 comprises a coupling magnet 31, and a rotation driving means (electric motor) 32 for rotating this coupling magnet 31 around the rotation shaft of the impeller 1. The coupling magnet 31 is opposed to a plurality of magnets 14 of the impeller 1, both magnets are magnetically coupled, and the impeller 1 rotates according the rotation of the magnet 14 according the rotation of the coupling magnet 31. A plurality of coupling magnets 31 are placed respectively symmetrically about a shaft 33, and fixed to the upper section of a rotor 35 supported by the shaft 33 through bearings 34, 34. This rotor 35 is a rotor similar to the one for the DC brushless motor, 36 indicates a winding and 37 a stator. It should be appreciated that g is a gap formed between a bottom plate 23 and the coupling magnet 31.

The control means for rotating speed are different according to the type of rotation driving means (electric motor) 32; in case where rotation driving means (electric motor) 32 is a DC motor, the rotating speed shall be controlled by a switching such as Pulse Width Modulation or the like, and in case of adopting an AC motor, it shall be controlled by an inverter circuit respectively, and the control means for rotating speed shall be installed integrally with or separately from the rotation driving means (electric motor) 32.

Further, in the embodiment shown in FIG. 1, a magnetic attraction force adjustment means 4 is interposed between the casing 2 and the magnetic driving means 3. In the drawing, the magnetic attraction force adjustment means 4 is composed of a spacer 42 interposed detachably between a support plate 41 of the casing 2 and an outlier section 38 of the magnetic driving means 3, or between the support plate 41 and the bottom face of the casing 2, and the support plate. The magnetic attraction force between the magnet 14 of the impeller 1 and the coupling magnet 31 of the magnetic driving means 3 is to be adjusted by adjusting the distance between the both magnets through attachment/detachment of the spacer 42. It should be appreciated that the magnetic attraction force between the both magnets may be adjusted, not by the spacer, but by composing the coupling magnet 31 with an electromagnet and regulating the exciting current thereto.

In case of using the blood pump according to the application as implanted type integral heart or ventricular assist device, the whole system is composed of a blood pump implanted in an organism, a percutaneous electric transmission path, an external power source and a system control means; hereinafter, an example of animal experiment as ventricular assist device to be used with an organic heart.

A blood pump is implanted in a way to bypass the organic heart (heart ventricle, to be precise). Whereby, it is intended to mitigate the load of an affected heart for a predetermined period and restore meanwhile the heart disease, and this period is about 6 months for erectile cardiomyopathy and about 2 years in case of ischemic cardiomyopathy. The implantation is performed with a pair of pumps, one (right pump) being implanted between the right heart ventricle and the pulmonary artery, and the other (left pump) between the left heart ventricle and the aorta.

Through the bypass implantation of blood pump, the right pump will receive a cyclic pressure difference of about 0 to 50 mmHg, and the left pump that of about 0 to 100 mmHg, respectively 70 to 100 times per minute. Here, the pressure means the pressure difference at the suction inlet 24 and delivery outlet 25 of the pump, and a repetition of this pressure difference by 70 to 100 times per minutes means that the pressure difference will be repeated by the number of times of organic heart pulsation.

Thus, the blood pump which is a centrifugal pump generating a continuous flow generates a pulsatile flow so long as the organic heart functions. In short, it is because the centrifugal pump maintains a high flow rate (corresponding to the heart systolic) when the pressure difference becomes small, while it ejects a low flow rate (corresponding to the heart diastole) when the pressure difference becomes large.

Figure 4:
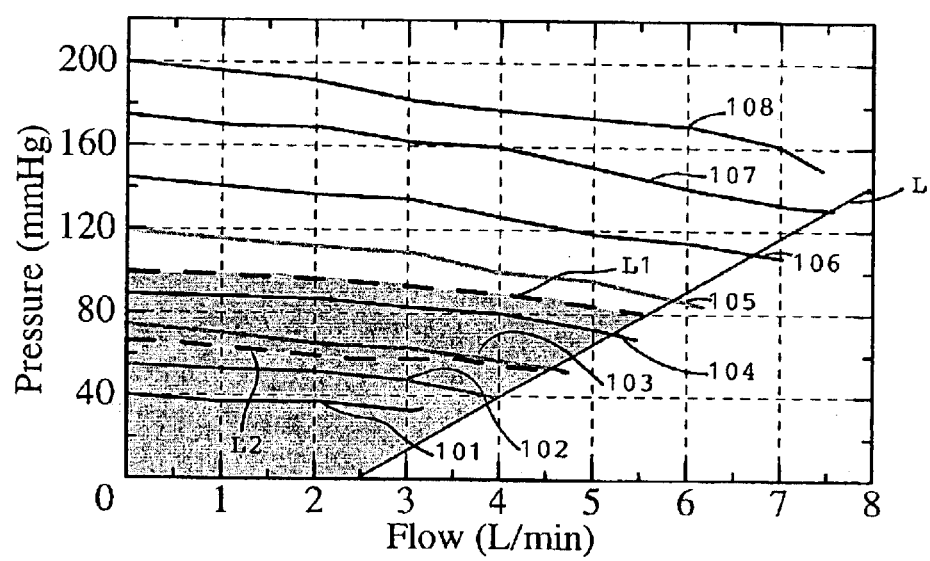
FIG. 4 is a graph showing the position of an impeller in a casing in the relation between rotating speed of impeller, blood flow rate and pressure difference.

Now, FIG. 4 is a graph showing the position of an impeller 1 in a casing 2 in the relation between rotating speed of impeller, blood flow rate and pressure difference, the Y-axis indicates the pressure difference value, while the X-axis the blood flow rate.

In this graph, 101, 102, 103, 104, 105, 106, 107, 108 indicate respectively the position of the impeller 1 in the casing 2 when the rotating speed of the impeller is 1200 RPM, 1400 RPM, 1600 RPM, 1800 RPM, 2000 RPM, 2200 RPM, 2400 RPM, 2600 RPM. In the left area of the slant line L in the graph, the range above the upper dot line L1 indicates the top contact, namely, a state where an upper end pivot shaft 16 of the impeller 1 is in contact with the bearing surface of an upper pivot bearing 26. While in the range under the lower dot line L2, it shows the bottom contact, namely, a state where the lower end pivot shaft 17 is in contact with the bearing surface of a lower pivot bearing 27.

And in the area between the upper dot line L1 and the lower dot line L2, it shows the case where the impeller 1 is levitated.

Based on the graph, for a required blood flow rate, the rotating speed of impeller necessary for the levitation of the impeller 1 or for the maintenance of top contact can be obtained.

Figure 5:
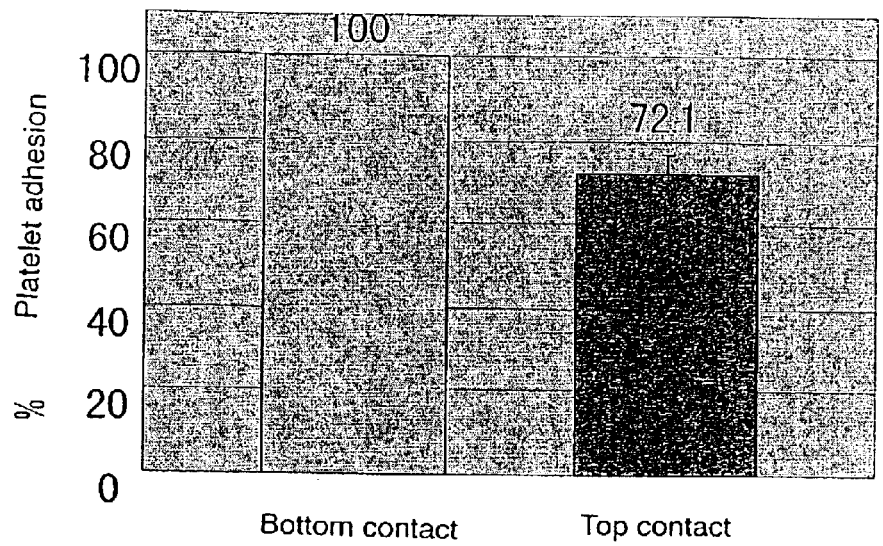
FIG. 5 is a graph showing the variation of platelet adhesion rate according to the position of the impeller.
Figure 5:
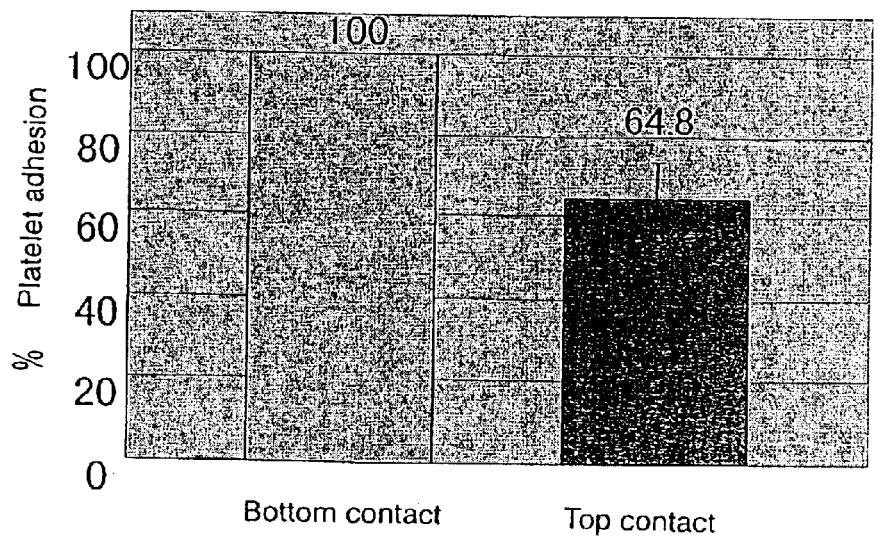

Now, in case of requiring a blood flow rate of slightly higher than 5 litters per minute, the impeller 1 shows the leviation state with a rotating speed of impeller 1600 RPM, and if the rotating speed is increased for instance to 1800 RPM, the impeller 1 shown the state of top contact. It should be appreciated that, as mentioned above, in the relation between the pressure difference and the flow rate, the flow rate decreases when the pressure difference increases, and on the contrary, the flow rate increases when the pressure difference decreases. In case of the rotating speed of the impeller=1600 RPM, a pressure difference of around 50 mmHg will be required to obtain a blood flow rate of slightly higher than 5 litters per minute. If the pressure difference is equal or inferior to this, a predetermined flow rate can not be obtained. Thus, taking the aforementioned graph as indicator, it is possible to know the rotating speed that allows to maintain the levitation state or top contact state, and the thrombosis prevention or other objects of the invention of the application can be attained by keeping the impeller in the levitation state or top contact state through the input of this rotating speed in the control means for rotating speed. As shown in the graph of FIG. 5, the thrombosis prevention effect is particularly pronounced. FIG. 5(*a*) is a graph comparing the adhesion of platelet to the bottom face of the impeller 1, for the case of bottom contact and for the case of top contact.

The adhesion of platelet to the bottom face of the impeller 1 in case of top contact has reduced by 27.9% compared to the case of bottom contact.

Moreover, FIG. 5(*b*) is a graph comparing the adhesion of platelet to the bottom face of the casing 2, for the case of bottom contact and for the case of top contact.

The adhesion of platelet to the bottom face of the casing 2 in case of top contact has reduced by 35.2% compared to the case of bottom contact.

Now, the aforementioned pressure difference is generated according to the pulsation of the organic heart in the casing 2 by the operation of the organic heart, producing a pressure difference between the upper section and the lower section of the impeller. On the other hand, as mentioned above, a clearance of 0.6 mm is formed between the upper end of the pivot shaft 16 and the bearing surface of the upper pivot bearing 26. Consequently, the impeller rotating in the casing moves up and down even if the rotating speed does not change. Furthermore, as the curvature radius R of the bearing surface of the pivot bearings 26, 27 is set to two times of the curvature radius r of the pivot shafts 16, 17, when the pump blood ejection rate differentiates the suction and discharge quantity while being synchronized with organic hart pulsation, the impeller titubates (swerves).

Such up and down motion, titubation (swerve) fluidizes blood stagnation portions in a casing, contributing to prevent thrombosis from occurring.

In an experiment, six pumps were implanted in the left heart ventricle and 5 pumps in the right heart ventricle, and operated for one to six months, for observing no thrombosis generating in the casing. In this experiment, the organic heart pulsation was 70 to 100 times per minute; consequently, it seems that the up and down motion, titubation (swerve), of the impeller was also 70 to 100 times per minute, and changes occurred also 70 to 100 times per minute at blood stagnation portions in the casing.

It should be appreciated that, in addition to the movement of the impeller, the blood fluidization at the casing bottom due to the generation of voids between the lower end of the pivot shaft and the bearing surface of the lower pivot bearing by the levitation or top contact of the impeller also contributes to control the thrombosis.

Though an example due to the organic heart pulsation was described for the aforementioned up and down motion, titubation (swerve), in the impeller, the same can also be realized by continuously changing the magnetic attraction force between the magnet of the impeller and the coupling magnet by the magnetic attraction force adjustment means.

The invention of the present application permit to obtain a small and light blood pump that can control the thrombosis by the composition/function described hereinabove, and moreover, endure a prolonged use.

What is claimed is:

1. A centrifugal blood pump comprising:

a centrifugal impeller including at least one magnet embedded the centrifugal impeller, a casing having a suction inlet and a delivery outlet and rotatably encasing the impeller, a magnetic drive means for rotating the impeller by magnetically acting from outside of the casing on a said at least one magnet, a magnetic attraction force adjustment means for adjusting the attraction force by the magnetic action, a control means for rotating speed of said magnetic drive means, and a pair of pivot bearings for supporting pivots at both ends of the impeller rotation shaft, wherein the distance between bearing faces of said both pivot bearings is set longer than the length of the rotation shaft of the impeller and the rotation speed of the impeller is controlled to a predetermined speed by said control means for rotating speed so as to levitate the impeller in the blood flow in the casing and to prevent the pivots at both ends of the rotation shaft of the impeller from contacting the bearing faces of said both pivot bearings.

2. The blood pump of claim 1, wherein the difference between the distance between the bearing faces of said both pivot bearings and the length of the rotation shaft of the impeller is set to 0.4 mm or longer.

3. The blood pump of claim 1, wherein the casing and impeller are formed of titanium or titanium alloys, and the surface roughness of titanium or titanium alloys at the points in contact with blood in the casing or impeller is polished to 0.5 micron or less.

4. The blood pump of claim 1, wherein the suction inlet is composed of a pipe made of titanium or titanium alloys having a bent section and connected to the casing upper section, and the surface roughness of the pipe inner surface be polished to 0.5 micron or less.

5. The blood pump of claim 1, wherein the bearing surface of the pair of pivot bearings supporting the pivots at both ends of the rotation shaft of the impeller are formed of ultra high polymer material.

6. The blood pump of claim 1, wherein the pivots at both ends of the rotation shaft of the impeller are formed from ceramics.

7. The blood pump of claim 1, wherein a curvature of the bearing surface of the pivot bearing section is set larger than the curvature of the pivot of the rotation shaft of the impeller.

8. The blood pump of claim 2, wherein the casing and impeller are formed of titanium or titanium alloys, and the surface roughness of titanium or titanium alloys at the points in contact with blood in the casing or impeller is polished to 0.5 micron or less.

9. The blood pump of claim 2, wherein the suction inlet is composed of a pipe made of titanium or titanium alloys having a bent section and connected to the casing upper section, and the surface roughness of the pipe inner surface be polished to 0.5 micron or less.

10. The blood pump of claim 3, wherein the suction inlet is composed of a pipe made of titanium or titanium alloys having a bent section and connected to the casing upper section, and the surface roughness of the pipe inner surface be polished to 0.5 micron or less.

11. The blood pump of claim 2, wherein the bearing surface of the pair of pivot bearings supporting the pivots at both ends of the rotation shaft of the impeller are formed of ultra high polymer material.

12. The blood pump of claim 3, wherein the bearing surface of the pair of pivot bearings supporting the pivots at both ends of the rotation shaft of the impeller are formed of ultra high polymer material.

13. The blood pump of claim 4, wherein the bearing surface of the pair of pivot bearings supporting the pivots at both ends of the rotation shaft of the impeller are formed of ultra high polymer material.

14. The blood pump of claim 2, wherein the pivots at both ends of the rotation shaft of the impeller are formed from ceramics.

15. The blood pump of claim 3, wherein the pivots at both ends of the rotation shaft of the impeller are formed from ceramics.

16. The blood pump of claim 4, wherein the pivots at both ends of the rotation shaft of the impeller are formed from ceramics.

17. The blood pump of claim 5, wherein the pivots at both ends of the rotation shaft of the impeller are formed from ceramics.

18. The blood pump of claim 2, wherein a curvature of the bearing surface of the pivot bearing section is set larger than the curvature of the pivot of the rotation shaft of the impeller.

19. The blood pump of claim 3, wherein a curvature of the bearing surface of the pivot bearing section is set larger than the curvature of the pivot of the rotation shaft of the impeller.

20. The blood pump of claim 4, wherein a curvature of the bearing surface of the pivot bearing section is set larger than the curvature of the pivot of the rotation shaft of the impeller.

21. The blood pump of claim 5, wherein a curvature of the bearing surface of the pivot bearing section is set larger than the curvature of the pivot of the rotation shaft of the impeller.

22. The blood pump of claim 6, wherein a curvature of the bearing surface of the pivot bearing section is set larger than the curvature of the pivot of the rotation shaft of the impeller.

23. A centrifugal blood pump comprising:
   a centrifugal impeller including at least one magnet embedded in the impeller;
   a casing rotatably encasing the impeller and having a suction inlet and a delivery outlet, said suction inlet configured to protrude substantially parallel to an inner wall face of a slant section of the casing and a slant section of the impeller in order to prevent hemolysis;
   a magnetic drive means for rotating the impeller by magnetically acting from outside of the casing on said at least one magnet;
   a magnetic attraction force adjustment means for adjusting the attraction force by the magnetic action;
   a control means for a rotation speed of said magnetic drive means; and
   a pair of pivot bearings for supporting pivots at both ends of the impeller rotation shaft, wherein the distance between bearing faces of said pivot bearings is set longer than the length of the rotation shaft of the impeller;
   wherein the rotation speed of the impeller is configured to levitate the impeller in the blood flow in the casing such that the pivots at both ends of the rotation shaft of the impeller are prevented from contacting said bearing faces of said pivot bearings.

* * * * *

UNITED STATES PATENT AND TRADEMARK OFFICE
CERTIFICATE OF CORRECTION

PATENT NO. : 6,884,210 B2
DATED : April 26, 2005
INVENTOR(S) : Nose et al.

It is certified that error appears in the above-identified patent and that said Letters Patent is hereby corrected as shown below:

Column 8,
Line 57, delete "a" in front of the word "said".

Signed and Sealed this

Nineteenth Day of July, 2005

JON W. DUDAS
*Director of the United States Patent and Trademark Office*